United States Patent
Sandberg et al.

(10) Patent No.: US 7,623,249 B2
(45) Date of Patent: Nov. 24, 2009

(54) AUTOMATED PRODUCT PROFILING APPARATUS AND PRODUCT SLICING SYSTEM USING SAME

(75) Inventors: Glenn Sandberg, Lockport, IL (US); Scott A. Lindee, Mokena, IL (US); Salvatore Lamartino, Orland Park, IL (US); Robert Bania, Orland Park, IL (US)

(73) Assignee: Formax, Inc., Mokena, IL (US)

( * ) Notice: Subject to any disclaimer, the term of this patent is extended or adjusted under 35 U.S.C. 154(b) by 0 days.

(21) Appl. No.: 12/267,402

(22) Filed: Nov. 7, 2008

(65) Prior Publication Data

US 2009/0064833 A1   Mar. 12, 2009

Related U.S. Application Data

(63) Continuation of application No. 11/100,720, filed on Apr. 7, 2005, now Pat. No. 7,450,247, which is a continuation of application No. 09/959,876, filed as application No. PCT/US00/10691 on Apr. 20, 2000, now Pat. No. 6,882,434.

(60) Provisional application No. 60/130,208, filed on Apr. 20, 1999.

(51) Int. Cl.
| | |
|---|---|
| *G01B 11/24* | (2006.01) |
| *G01B 11/30* | (2006.01) |
| *G01N 9/04* | (2006.01) |
| *G01N 21/86* | (2006.01) |
| *G06M 7/00* | (2006.01) |
| *H01J 40/14* | (2006.01) |
| *G01V 8/00* | (2006.01) |
| *A23N 4/04* | (2006.01) |
| *B26D 5/00* | (2006.01) |
| *A22C 18/00* | (2006.01) |
| *A22C 21/00* | (2006.01) |
| *A22C 25/00* | (2006.01) |

(52) U.S. Cl. ............... 356/601; 250/223 R; 250/559.22; 99/537; 83/364; 452/157

(58) Field of Classification Search ...................... None
See application file for complete search history.

(56) References Cited

U.S. PATENT DOCUMENTS 3,527,083 A    9/1970  Hensgen
(Continued)

FOREIGN PATENT DOCUMENTS

DE          37 14199 C2    11/1987
(Continued)

OTHER PUBLICATIONS

Thurne, "IBS 2000 Visions Slicer," 2 pages.
Dynamic Control Systems, "L4 3D Snapshot Scanner," The Next Generation of 3-D Snapshot Scanning, 4 pages.
Lumetch, "Automatic Trimming Machine for Fish Fillets," 6 pages.
DSI Stein, "The Portioner," Automated Waterjet Cutting and Portioning System, 6 pages.
Townsend, "Townsend Integrated Bacon Network," 6 pages.

*Primary Examiner*—Michael A Lyons
*Assistant Examiner*—Gordon J Stock, Jr.
(74) *Attorney, Agent, or Firm*—Erickson Law Group, PC

(57) ABSTRACT

A system, suitable for high-speed operation, by which raw product (45), such as a slab of meat, can be accurately processed, such as by slicing into segments of desired weight, comprises a product profiling apparatus (15). The product profiling apparatus (15) measures the profile of the physical process. The product profiling apparatus (15) includes line lasers (75, 85) for directing a line of light across the upper and lower surfaces of the product (45) and visual image cameras (80, 90) directed toward the profile surface to capture, at fixed increments, the product profile. The product may also be weighed and the product density determined from the overall profile measurements. A controller (150) receives this data, and instructs the physical process accordingly.

19 Claims, 6 Drawing Sheets

U.S. PATENT DOCUMENTS

| | | | |
|---|---|---|---|
| 3,730,742 A | 5/1973 | Burton et al. | |
| 3,751,873 A | 8/1973 | Toby | |
| 4,038,531 A | 7/1977 | Loe, Jr. | |
| 4,114,492 A | 9/1978 | Skidmore | |
| 4,136,504 A | 1/1979 | Wyslotsky | |
| 4,208,933 A | 6/1980 | Skidmore | |
| 4,279,513 A | 7/1981 | Tucker | |
| 4,324,335 A | 4/1982 | Conway et al. | |
| 4,532,840 A | 8/1985 | Antonissen | |
| 4,557,019 A | 12/1985 | Van Devanter et al. | |
| 4,572,044 A | 2/1986 | Antonissen | |
| 4,580,475 A | 4/1986 | Antonissen | |
| 4,624,367 A | 11/1986 | Shafer et al. | |
| 4,855,608 A | 8/1989 | Peterson, II | |
| 4,905,512 A | 3/1990 | Hayashi | |
| 4,959,553 A | 9/1990 | Yamada et al. | |
| 4,962,568 A | 10/1990 | Rudy et al. | |
| 5,028,799 A | 7/1991 | Chen et al. | |
| 5,117,717 A | 6/1992 | Mally | |
| 5,163,865 A | 11/1992 | Smith | |
| 5,184,733 A | 2/1993 | Arnarson et al. | |
| 5,226,241 A | 7/1993 | Goodwin | |
| 5,372,540 A | 12/1994 | Burch et al. | |
| 5,450,333 A * | 9/1995 | Minami et al. | 700/167 |
| 5,481,466 A * | 1/1996 | Carey | 700/167 |
| 5,745,237 A | 4/1998 | Yahiro et al. | |
| 5,774,220 A | 6/1998 | Wienecke | |
| 5,902,177 A * | 5/1999 | Tessier et al. | 452/156 |
| 5,937,080 A * | 8/1999 | Vogeley et al. | 382/110 |
| 5,960,104 A | 9/1999 | Conners et al. | |
| 6,137,577 A | 10/2000 | Woodworth | |
| 6,177,999 B1 | 1/2001 | Wurz et al. | |
| 6,272,437 B1 | 8/2001 | Woods et al. | |
| 6,407,818 B1 * | 6/2002 | Whitehouse | 356/627 |
| 6,610,953 B1 * | 8/2003 | Tao et al. | 209/577 |
| 6,983,678 B2 * | 1/2006 | Wattles et al. | 83/102 |
| 7,373,217 B2 * | 5/2008 | Young | 700/127 |
| 7,433,059 B2 * | 10/2008 | van der Knijff et al. | 356/614 |

FOREIGN PATENT DOCUMENTS

| | | |
|---|---|---|
| DE | G 8706 145.7 | 2/1988 |
| DE | 4001298 A1 | 7/1991 |
| DE | 4037383 A1 | 5/1992 |
| DE | 4301538 A1 | 7/1994 |
| DE | 19604254 A1 | 8/1997 |
| DE | 19741730 A1 | 4/1999 |
| EP | 0500478 | 2/1992 |
| EP | 0227701 B1 | 3/1992 |
| EP | 1044770 A1 | 10/2000 |
| EP | 1046478 A1 | 12/2000 |
| FR | 2 627 423 A1 | 8/1989 |
| GB | 991972 | 5/1965 |
| GB | 1507683 | 4/1978 |
| GB | 2099609 | 12/1982 |
| GB | 2 149 650 | 6/1985 |
| JP | 1-132333 | 5/1989 |
| JP | 7-184534 | 7/1995 |
| JP | 09029693 A | 2/1997 |
| JP | 11230728 A | 8/1999 |
| WO | WO 89/08983 | 10/1989 |
| WO | WO 91/08439 A1 | 6/1991 |
| WO | WO 93/22114 A1 | 11/1993 |
| WO | WO 93/24287 | 12/1993 |
| WO | WO 95/21375 | 1/1995 |
| WO | WO 98/35797 | 8/1998 |
| WO | WO 98/42196 | 10/1998 |
| WO | WO 99/06796 A1 | 2/1999 |
| WO | WO 99/47885 | 9/1999 |
| WO | WO 00/61338 | 10/2000 |

* cited by examiner

AUTOMATED PRODUCT PROFILING APPARATUS AND PRODUCT SLICING SYSTEM USING SAME

CROSS-REFERENCE TO RELATED APPLICATIONS

This application is a continuation of U.S. Ser. No. 11/100,720, filed Apr. 7, 2005, now U.S. Pat. No. 7,450,247 which is a continuation of U.S. Ser. No. 09/959,876, filed Feb. 19, 2002, now U.S. Pat. No. 6,882,434 which is a national stage application of PCT/US00/10691, filed Apr. 20, 2000, which claims priority from U.S. Provisional Application No. 60/130,208, filed Apr. 20, 1999.

STATEMENT REGARDING FEDERALLY SPONSORED RESEARCH OR DEVELOPMENT

Not Applicable

BACKGROUND OF THE INVENTION

The present invention relates to an apparatus for determining the profile of a product that is to undergo a subsequent physical process. The subsequent physical process is one in which the product profile is needed to insure proper processing of the product.

In the particular embodiment disclosed herein, the specific subsequent physical process includes slicing the product into individual slices on a slicing machine. Such slicing machines are principally, but not exclusively, used for slicing food products such as cheese, meat and pressed or molded meat products.

Typically such slicing machines include a rotating blade and a product feeder that drives the product forward towards the blade so that successive slices are cut from one face of the product. The distance through which the product is advanced between successive cuts of the blade determines the thickness of the slices. Where the product is of uniform shape and density, it may be sufficient to use a single predetermined slice thickness to give a slice or group of slices of the required weight. Further, it may be sufficient to provide an output scale proximate the output side of the blade to measure the current weight of the slice to product and adjust the thickness of the subsequent slice(s) to make the desired unit weight.

In general, however, variations in the shape and density of the product mean that the weight of a slice of a given thickness varies. A previous approach to dealing with this variation is described and claimed in U.S. Pat. No. 4,428,263, which is hereby incorporated by reference. That patent describes a process in which an automatic slicing machine is programmed to vary the thickness of the slices in accordance with a typical weight distribution for the product.

It has also been proposed to make some determination of the cross-sectional area of the product as it is cut. One such system is purportedly disclosed in U.S. Pat. No. 5,136,906, titled "Slicing Machine", and assigned to Thurne Engineering Co., Ltd. According to that patent, a slicing machine for cutting slices from a product includes a camera arranged to view a cut face of the product, boundary recognition apparatus arranged to process image signals from the camera to determine a boundary of the cut face, calculating apparatus arranged to calculate a parameter characteristic of the cut face from image data corresponding to regions of the cut face within the boundary, and control signal generating apparatus arranged to generate a control signal to control the operation of the slicer in accordance with the determined parameter.

Although the foregoing system may be suitable for low-throughput slicing machines, it is significantly less suitable for high-speed slicing machines, such as those available from Formax, Inc., of Mokena, Ill., under the brand name S-180.TM.. First, by calculating the product profile at the cut face, a very limited amount of processing time is available to perform the calculations that are necessary to ensure the proper thickness of each slice before the cut face must again be imaged for processing the thickness of the next slice. Second, substantial measurement inaccuracies may result from shadowing effects resulting from the relative positions of the illumination source, cut face, and slicing machine components—a problem not addressed in the '906 patent. Third, further measurement inaccuracies are introduced by the apparent assumption that the profiles at the bottom and a side of the product are linear. Finally, by attempting to measure the product profile at the cut face, substantial inaccuracies may be introduced due to the presence of scrap product. One of the goals of the apparatus described in the '906 patent is to remove the inaccuracies introduced by the scrap product. However, by addressing this problem at the cut face, the apparatus of the '906 must necessarily introduce a further level and higher degree of image processing.

The present inventors have addressed many of the foregoing problems inherent in the product profiling operations of prior art apparatus. To this end, they have developed an accurate and cost-effective product profiling apparatus that is suitable for use, for example, in connection with high-speed product slicing machines.

BRIEF SUMMARY OF THE INVENTION

An apparatus for acquiring a profile of a product for use in subsequent processing of the product is set forth. The apparatus includes a scanning chamber for accepting the product and one or more product drives that are operable to drive the product through the scanning chamber prior to delivery of the product to a subsequent product processor. The apparatus also includes a vision system disposed to acquire visual information relating to the profile of the product prior to delivery of the product to a subsequent product processor and a control system connected for control of the vision system and operating to convert the information received from the vision system into a format suitable for use by a subsequent product processor.

DETAILED DESCRIPTION OF THE INVENTION

Figure 1:
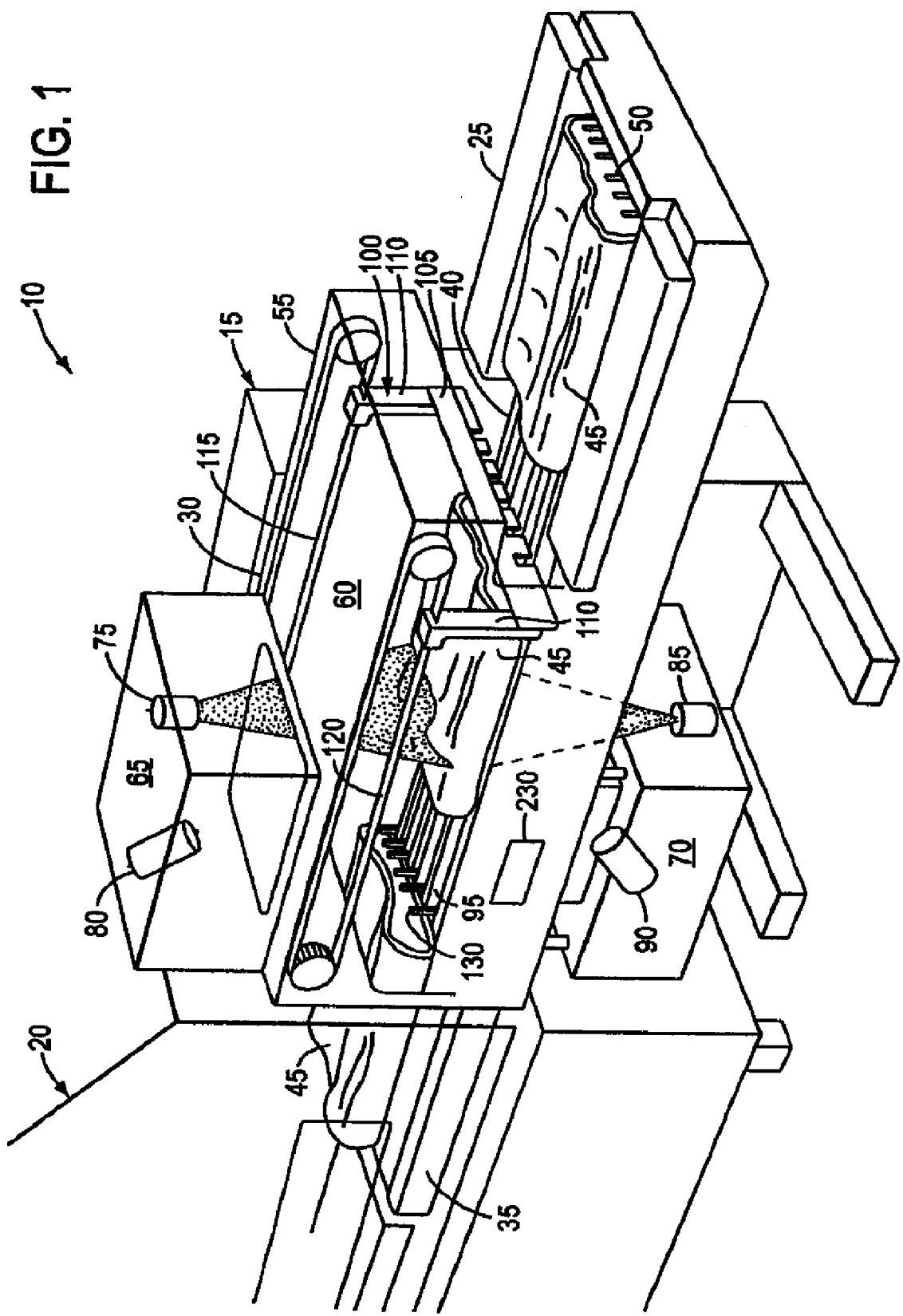
FIG. 1 is a perspective view of a product processing system constructed in accordance with one embodiment of the present invention.

FIG. 1 illustrates a product processing system, shown generally at 10, that performs a physical process on a product in which the physical process is dependent on accurate measurement of the profile of the raw product. As shown, product processing system 10 is comprised of a product profiling apparatus 15 and a product processor 20. The product profiling apparatus 15 functions to measure the profile of the raw product and provide the profile information to the product processor 20 that, in turn, uses the information to accurately execute the physical process that is to be performed on the raw product.

In the illustrated embodiment, the acquisition of the product profile information is completed before the particular raw product undergoes physical processing in the product processor 20. Using the configuration shown in FIG. 1 in which the profiling apparatus 15 is disposed prior to the product processor 20, it is possible to acquire complete product profiles for several individual raw products before each of the raw products is provided to the input of the product processor 20. Additionally, if the profiling apparatus 15 is designed as a stand-alone apparatus, then the profiling apparatus 15 may be used to provide product profile information to a plurality of different product processors that are operating in either a time sequential or concurrent manner.

Generally stated, the profiling apparatus 15 is comprised of an input section 25, a scanning section 30, and an output section 35. The input section 25 includes a plurality of support bars 40 that are disposed to support the product 45 that is to be profiled. A plurality of upstanding fingers 50 extend through interstitial regions between the support bars 40. The fingers 50 engage a rear portion of product 45 and drive it into the scanning section 30. The fingers are arranged to be vertically above the support bars when moved in the driving direction and vertically beneath the bars when conducted in the return direction.

Scanning section 30 includes a housing 55 having an input end that is open to receive product 45 and an outlet end that is open to allow product 45 to exit therefrom. In the illustrated embodiment, housing 55 comprises a principal housing portion 60, an upper vision system housing 65, and a lower vision housing 70. The upper vision system housing 65 includes an upper vision system disposed therein. The upper vision system of the disclosed embodiment includes a vertically directed line laser 75 for illuminating one side of the product in a fixed plane traversed by the driven product and an associated camera 80 vertically angled for imaging the laser-illuminated contour of the product 45. Similarly, the lower vision system housing 70 includes a lower vision system disposed therein that is comprised of a line laser 85 and corresponding camera 90 for addressing the other side of the product. Each of the upper and lower vision system housings 65 and 70 includes an opening that is positioned to allow the respective vision system to view a product 45 passing through the principal housing 60. These openings may merely comprise cut out sections. Preferably, however, the openings are covered with a transparent material to form a window that mechanically isolates the vision system components from the components disposed in the principal housing 60 yet does not interfere with the vision system operation.

Although, for purposes of this overview description of the product profiling apparatus 15, with reference to the early Figures, a single line laser is shown for use in each of the upper and lower vision system housings 65 and 70, it is considered more preferable, as further discussed below with respect to a more detailed discussion of structure and operation of the system machinery, that each of the vision system housings contain two opposing line lasers for illuminating downwardly and across the product from opposed sides of the product. In instances of a considerably uneven profile and/or in the event of highly reflective surface characteristics, opposed sides illumination on the product provides for higher resolution camera imaging.

Within principal housing 60, product 45 is supported by a plurality of rounded support bars 95. These support bars 95 may be formed as extensions of support bars 40, or may be formed as a support component that is distinct from support bars 40. The number and diameter of the support bars 95 should be minimized to facilitate accuracy of the scanning measurements provided by the lower vision system. Most preferably, although not shown, the diameters of the support bars 95 are substantially reduced to a minimum where they cross the laser light line emanating from the lower vision system laser.

Product 45 is driven through the principal housing 60 by a product drive, shown generally at 100. In the illustrated embodiment, the product drive 100 is comprised of a product engagement member 105 that is disposed to engage a rear portion of product 45 and drive it along support rods 95 through the principal housing 60. Product engagement member 105 includes a plurality of slots that are disposed to allow concurrent operation of the fingers 50 and product engagement member 105 at the input end of the principal housing 60. A pair of upstanding members 110 are connected to opposite ends of the product engagement member 105. The upstanding members 110, in turn, are fastened to respective drive belts 115 and 120 to move the product engagement member 105 and corresponding product 45 through the principal housing 60. The drive belts 115 and 120 are preferably driven at a constant, precise velocity by, for example, a servo motor, a motor with a resolver, etc.

At the outlet end of the principal housing 60, the product 45 is engaged by another set of fingers 130 that extends through interstitial regions of support bars 95. Support bars 95 may be extended to the output section 35 or, alternatively, a further distinct set of support bars may be used to support the product 45 at the output section 35. Fingers 130 engage the rear portion of product 45 and drive it to the output section 35 and therefrom to the processing apparatus 20, which, in the disclosed embodiment, is a slicing machine.

Figure 2:
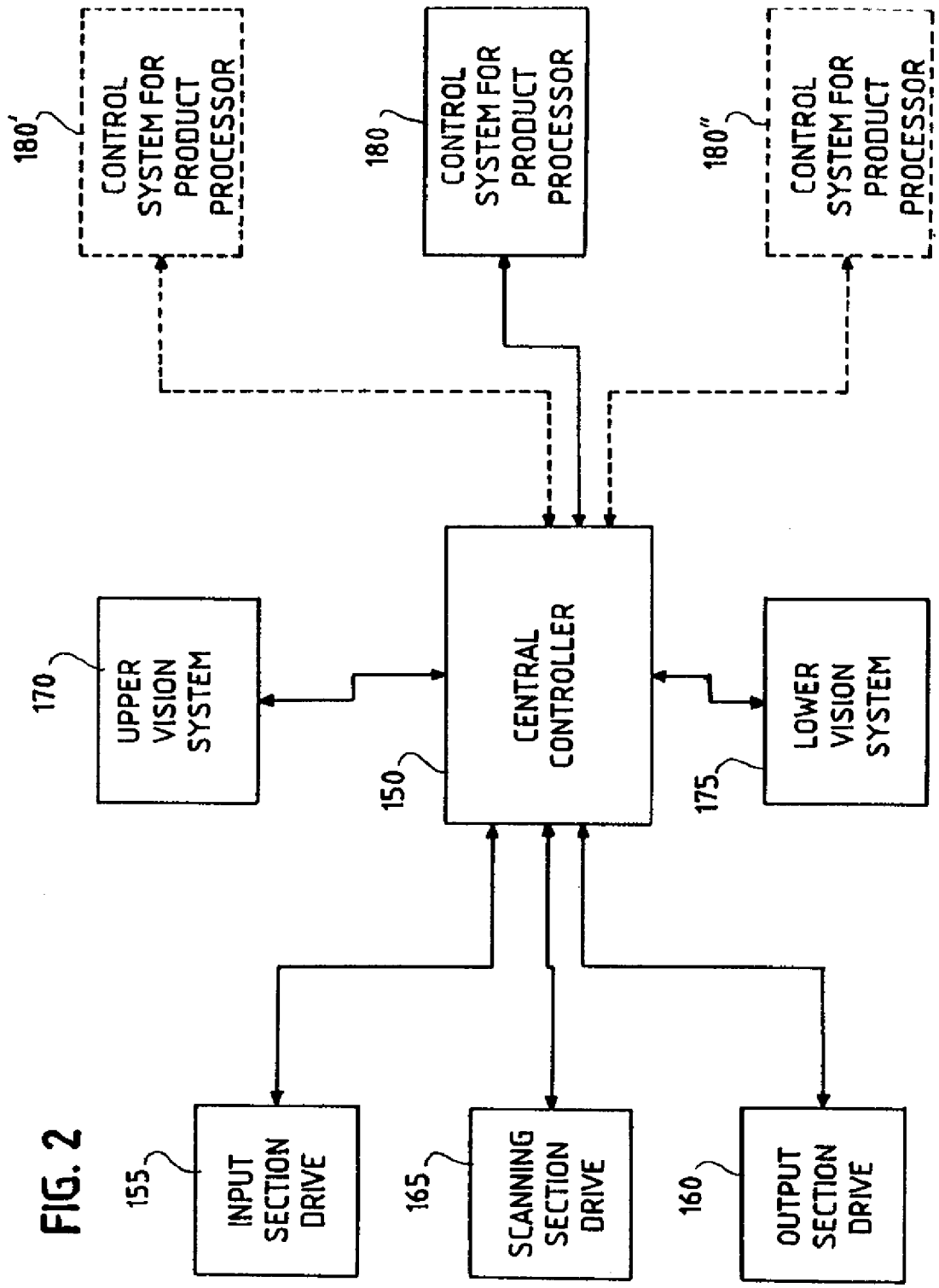
FIG. 2 is a schematic block diagram of one embodiment of a control system that may be used in the profiling apparatus of the system illustrated in FIG. 1.

FIG. 2 is a schematic block diagram of one embodiment of a control system suitable for controlled operation of product profiling apparatus 15. In the illustrated embodiment, the control system comprises a central controller 150 that is responsible for 1) controlling the drive mechanisms associated with various portions of the profiling apparatus 15; 2) coordinating the operation of the vision systems, including acquisition of the profile data; and 3) communicating the profile data to control systems for one or more product processors 20. To this end, the central controller 150 is connected to receive sensed signals from and provide motion control signals to each of the input and output section drives 155 and 160 and the scanning section drive 165. Similarly, the central controller 150 is connected to receive sensed signals from and provide scanning control signals to the upper and lower vision systems 170 and 175. Ultimately, the profile information acquired from the upper and lower vision systems 170 and 175 is communicated to the control system 180 of at least one product processor 20. The profile information may be communicated to the control system 180 in any one of a variety of processing states. For example, the central controller 150 may communicate raw profile data to the control system 180. Alternatively, or in addition, the central controller 150 may communicate the profile information after the raw data it acquires has been processed at the central controller 150 thereby relieving the control system 180 from much of the additional processing overhead associated with profile calculations.

If more than one product processor 20 is to be served by a single product profiling apparatus 15, then a method for tracking each product 45 through the system to insure that each of the product processors 20 receives the correct profile data must be provided. For example, each of the products 45 may be provided with a bar-code or other visual image marker that may be acquired or otherwise input to the central controller 150 as well as the particular control system 180, 180', 180" associated with the particular product processor 20 that is to slice the particular product. When the identity of the product 45 that is to be sliced by the product processor is determined by the respective control system 180, 180', 180", the particular control system may request the profile data associated with the identified product from the central controller 150.

Operation of the product profiling apparatus 15 can be described with respect to FIGS. 1 and 2. First, the product 45, shown here as a slab of bacon or the like, is provided at input section 25 where it is supported by support rods 40. Central controller 150 then activates input section drive 155 so that fingers 50 engage the rear portion of product 45 and drive it into the scanning section 30. Product engagement member 105 is preferably hinged to swing out of the way or otherwise glide over the upper surface of product 45 as it is moved through the opening at the input of the scanning section 30. The central controller 150 directs the scanning section drive 165 to operate so that the product engagement member 105 contacts the rear portion of product 45 and begins to drive product 45 through the interior chamber of the principal housing 55. Preferably, the product 45 is driven a small distance over support rods 95 before reaching the position in the principal housing 55 in which product scanning begins. This allows the product to settle upon the support rods 95 and against product engagement member 105 before scanning thereby increasing the accuracy of the resulting profile data.

In accordance with one embodiment of the profiling apparatus 15, a resolver or the like associated with the scanning section drive 165 generates control pulses corresponding to incremental movement of the product 45 over a fixed distance through the principal housing 55. These control pulses are used as synchronization signals that the central controller 150 uses to trigger the acquisition of a profile reading. Here, the profile readings are in the form of a visual image captured by the cameras 80 and 90 at fixed increments along the length of the product 45. The product profile is accentuated by directing a line of laser light across the upper and lower surfaces of the product 45. Accordingly, the interior of the principal housing 55 should be as dark as possible so that cameras 80 and 90 may detect the line projected by line lasers 75 and 85.

Figure 3:
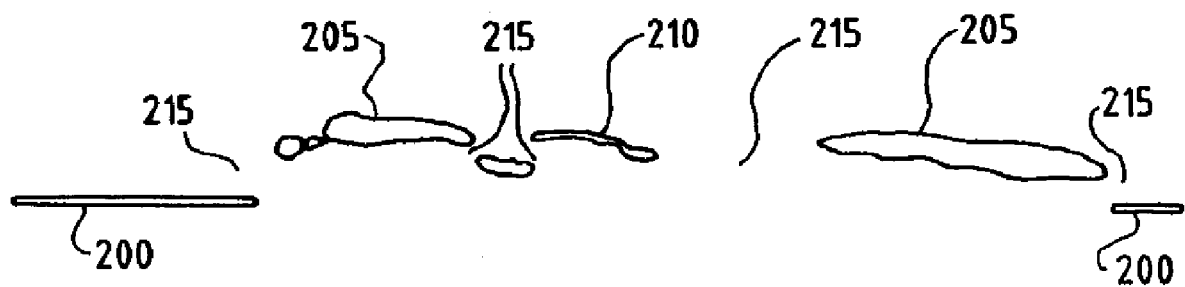
FIG. 3 is an exemplary image obtained by the upper vision system of the embodiment of the profiling apparatus illustrated in FIG. 1.

FIG. 3 is an exemplary image acquired by camera 80 of profiling apparatus 15. Although camera 80 is capable all of providing an image of 640.times.480 pixels, only a sub-portion of that entire available image is extracted by central controller 150 for further processing. As shown, the resulting image is comprised of linear end regions 200. The linear end regions are formed by reflection of the light from line laser 75 by a pair of reference reflectors that, preferably, are disposed to be even with the upper surfaces of support rods 95. There are a plurality of elevated, non-linear regions between linear regions 200. These non-linear regions correspond to the upper profile of product 45 that has been illuminated by line laser 75. By taking measurements of the vertical distance (e.g., the number of vertical pixels) between linear end regions 200 and the elevated, non-linear regions, it is possible to calculate the contour of the profile of the product at the position along the interior of principal housing 55 at which the image was acquired. By acquiring a number of such images along the length of product 45, an accurate representation of the upper profile of product 45 can be obtained. Similar images are concurrently acquired by camera 90 based on illumination of the lower portion of product 45 by line laser 85. As in the case of the upper profile measurements, linear reference regions are formed by reflection of the light from line laser 85 by a pair of reference reflectors. From the images of the upper and lower product surfaces that are acquired by the upper and lower vision systems 170 and 175, the central controller 150 can provide a substantially accurate data representation of the complete product profile to control system 180 of product processor 20.

Depending on the content of the product 45, the laser light impinging on the upper surface of product 45 may be dispersed in different manners. For example, if the product 45 is bacon or another fat-containing comestible, fatted regions, such as at 205 disperse the laser light to a greater degree than lean regions 210. As a result, a broader light band is formed at the fatted regions 205. Controller 150 may compensate for this dispersion by, for example, selecting the area of highest dark pixel concentration for the vertical measurement. Alternatively, a vertical distance measurement may be obtained by taking the average vertical distance of the uppermost vertical distance measurement and the lowermost vertical distance measurement.

As shown in FIG. 3, the light reflected from the surface of product 45 may be blocked from the view of the camera. These regions appear as void regions 215. In such regions, central controller 150 may be programmed to assume a linear transition of the surface contour. Since void regions 215 are generally of a very limited dimension, this assumption still provides for an accurate representation of the overall product profile. Similarly, an assumption that there is a linear transition of the surface contour at the regions of the lower surface of product 45 that are blocked by support rods 90 does not significantly diminish the accuracy of the profile measurements. To minimize any inaccuracies introduced by the presence of support rods 95, the number and diameter of support rods 90 should be minimized. Further, support rods 95 should have a generally round cross-section so that they generate obstructed or otherwise unusable regions of the profile image that are substantially equal in the length.

Once product 45 as been driven to the outlet portion of scanning section 30, the central controller 150 controls the output section drive 160 so that fingers 130 engage the rear portion of product 45 and drive it from the interior of scanning section 15 to output section 35. Product 45 may be removed by an operator from section 35 and provided to the input of a subsequent product processor 20. Alternatively, the output section 35 and corresponding output section drive 160 may be designed to drive product 45 into a loading position on the subsequent product processor.

Profiling apparatus 15 may include a digital scale 230 (shown schematically in FIG. 1) for weighing the product 45. The output of the digital scale may be provided to central controller 150. Central controller 150 may be programmed to calculate the overall volume of product 45 based on the profile measurements. Central controller 150 may then use the overall product value and the weight provided by the digital scale to calculate the average density of the product 45. The average density measurement may be used by a slicing machine, such as product processor 20, in combination with the profile measurements to calculate the product slice thicknesses that are required to make a particular weight, such as the weight of product slices that are to be provided in a single consumer package. Alternatively, one or more of the average density, overall volume, or product profile measurements/calculations may be executed by the control system 180 of the slicing machine.

Figure 4:
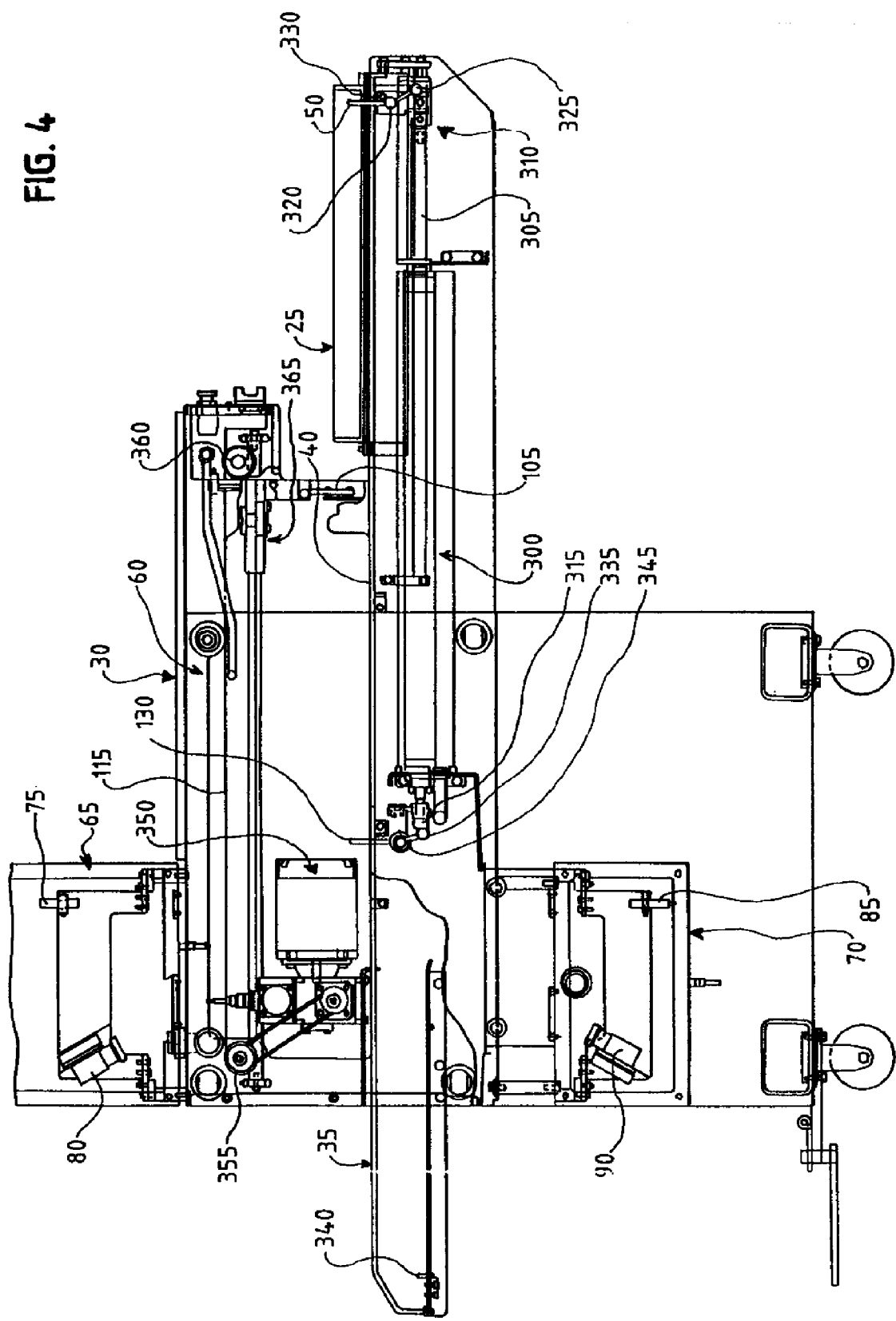
FIGS. 4 and 5 are cross-sectional views of one embodiment of a profiling apparatus that may be used in the system FIG. 1.
Figure 5:
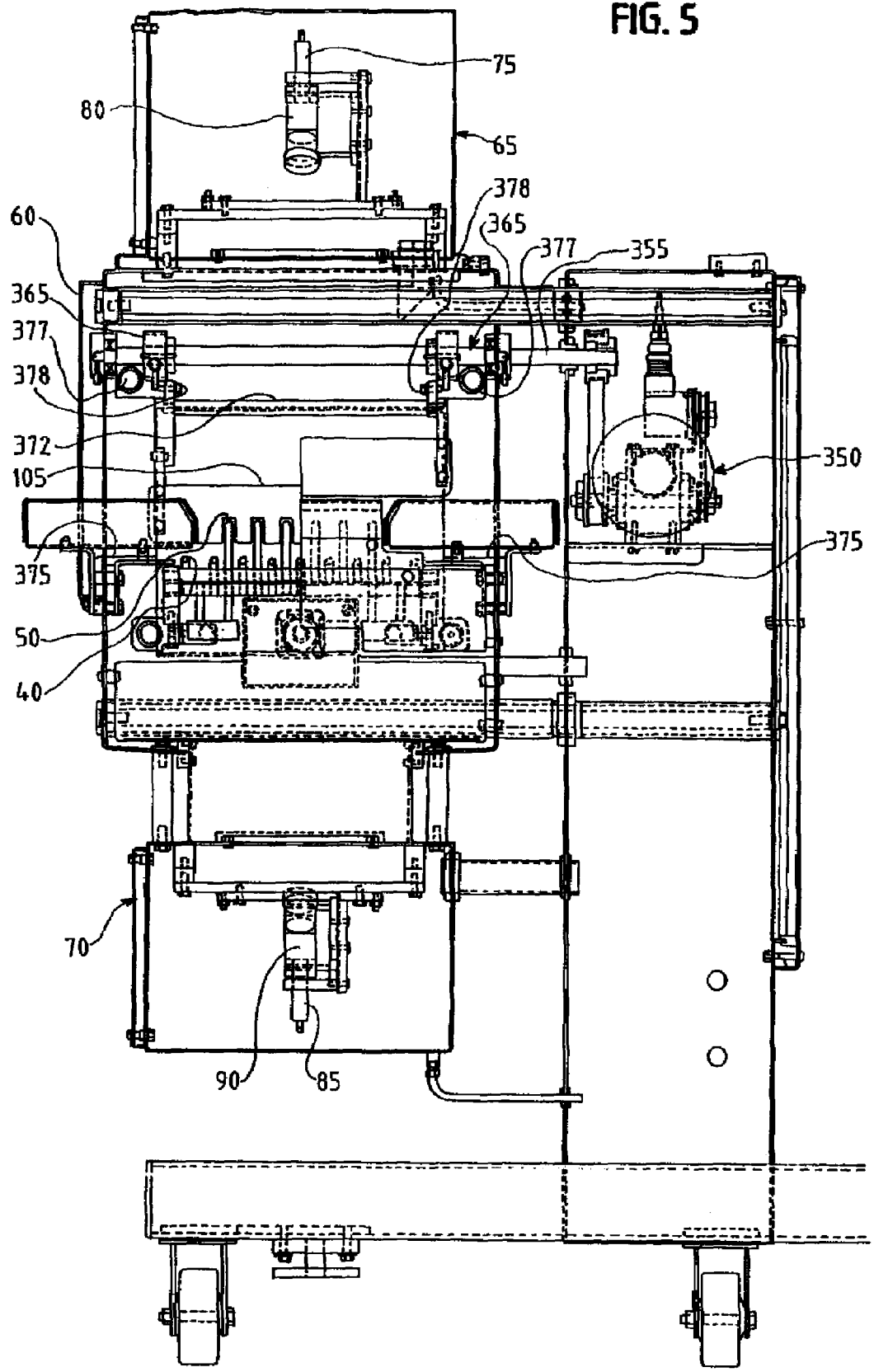

FIGS. 4 and 5 illustrate a specific embodiment of the profiling apparatus 15 in which like parts are similarly numbered. Of note in connection with the embodiment shown in these Figures are the drive mechanisms associated with input section 25, scanning section 30, and output section 35.

It has been found and is considered preferable that, rather than using a single line laser to illuminate a surface of the product as shown in FIG. 4, a pair of generally opposed lasers applying overlapping beams to cover that surface of the product can yield more profile data and better resolution in the camera image. This would be the case especially in instances where the product surface is quite irregular and/or contains large fatted regions since these situations tend to result in shadowing an/or blurring in the camera image. The more the profile data and the better the resolution in the camera image, the more definite and precise is the surface profile data, there being less need for averaging or extrapolation.

In the case of using more than one line laser in each of the vision system housings above and below the product, the lasers are preferably disposed on opposite sides of the product and projecting their beams down onto and across the product. The camera position generally does not change. In this way, a triangulated approach to capture of the surface profile on both respective sides of the product is utilized.

As illustrated, the drive mechanisms associated with the input section 25 and output section 35 are interrelated. More particularly, the drive mechanisms are comprised of a single, dual-ended pneumatic actuator, shown generally at 300 that is mounted below support rods 40 (the support rods throughout are continuous and formed as a single set of rods). Actuator 300 includes a piston rod 305 having a first end connected to a first finger engagement assembly 315 and a second end connected to a second finger engagement assembly 310. Finger engagement assembly 310 includes the fingers 50 thereon while finger engagement assembly 315 includes the fingers 130 thereon. Fingers 50 are disposed on a pivot rod 320 along with one or more counterbalance mechanisms 325. The counterbalance mechanisms 325 urge fingers 50 to rotate about a horizontal axis defined by pivot rod 320 until fingers 50 engage one or more stop members 330. The one or more stop members 330 are disposed to the stock fell rotation of fingers 50 when they are in an upright position. This arrangement allows fingers 50 to slide under a successive product 45 disposed on the input section 25 as the fingers are driven back to the home position after delivering a previous product 45 to the scanning section 30.

A similar arrangement is provided for finger assembly 315 disposed at the first end of piston rod 305. Here, however, the one or more counterbalance mechanisms 335 of the finger assembly 315 are positioned to engage a further stop member 340 at the output position of the output section 35. As the fingers 130 drive product 45 along output section 35, counterbalance mechanisms 335 are driven into engagement with the further stop mechanisms 340. This causes the fingers 130 to rotate about a horizontal axis defined by pivot rod 345 which assists in driving the product 45 from output section 35 to, for example, the input of a slicing machine.

In the embodiment shown in FIGS. 4 and 5, the scanning section drive includes motor 350 that is connected to rotate drive roller 355. Drive roller 355, in turn, drives belts 115 and 120, each of which extends between drive roller 355 and idle roller 360. Securement mechanisms 365 are connected to upstanding members 110 (shown in FIG. 5) to secure upstanding members 110 and product engagement member 105 with drives belts 115 and 120. The securement mechanisms 365 are connected to one another by a strut 372 to enhance the rigidity of the overall drive mechanism. Additionally, securement mechanisms 365 each engage respective guide rods 377 that extend along the length of the transport path along which the product engagement member 105 moves product 45 through scanning section 30. Preferably, securement members 365 each include a pivoted connection 378 that allows the product engagement member 105 to glide over the upper surface of a product 45 disposed in the scanning section 30 as member 105 is returned to its home position after driving a product from the scanning section 30. Alternatively, the product engagement member 105 may be actively moved by, for example, an actuator, so that its movement to the home position is not obstructed by the product 45.

Figure 6:
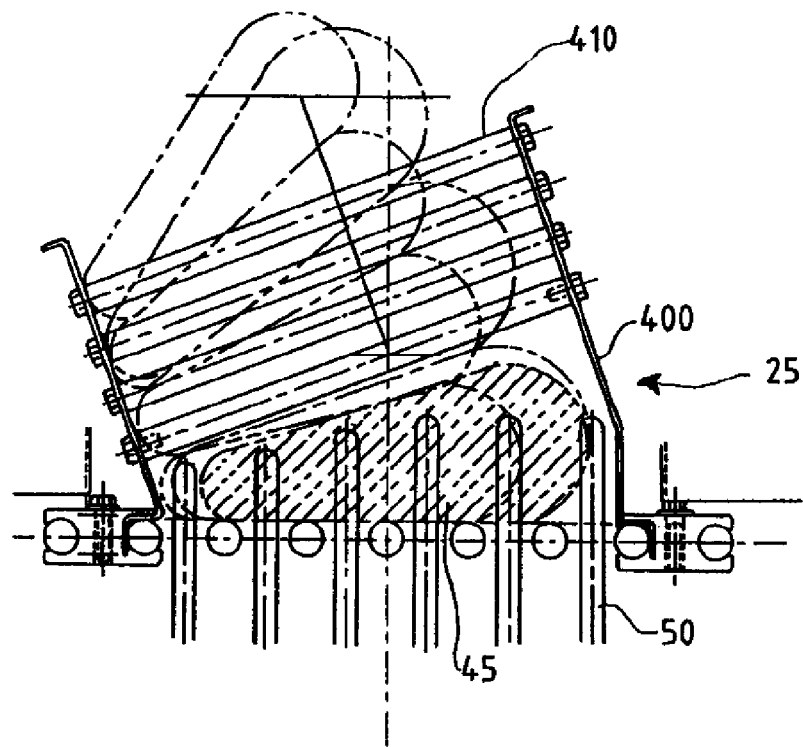
FIG. 6 is a schematic cross-sectional view showing an input stacker.

To further facilitate and enhance continuous, automated running of the invention product processing system, the product is preferably supplied to the input section 25 from a stacked input. FIG. 6 illustrates a specific embodiment of a vertically extending stacker 400, in the form of a chute the walls of which are defined by columns of rollers 410. The lower end of the chute is immediately above, and opens onto, the input section 25. The upper end of the chute extends above and angles away from the input section. The chute defines a gravity-drop passage in which a plurality of the products can be stacked one on top of the other for successive and automatic loading onto the input section 25. After each previous, underlying product has landed on the input section support bars and been passed from beneath the chute into the scanning section 30 by the fingers 50, the next product in the stack drops onto the input section support bars such that the system is automatically loaded for a continuous running operation.

Figure 7:
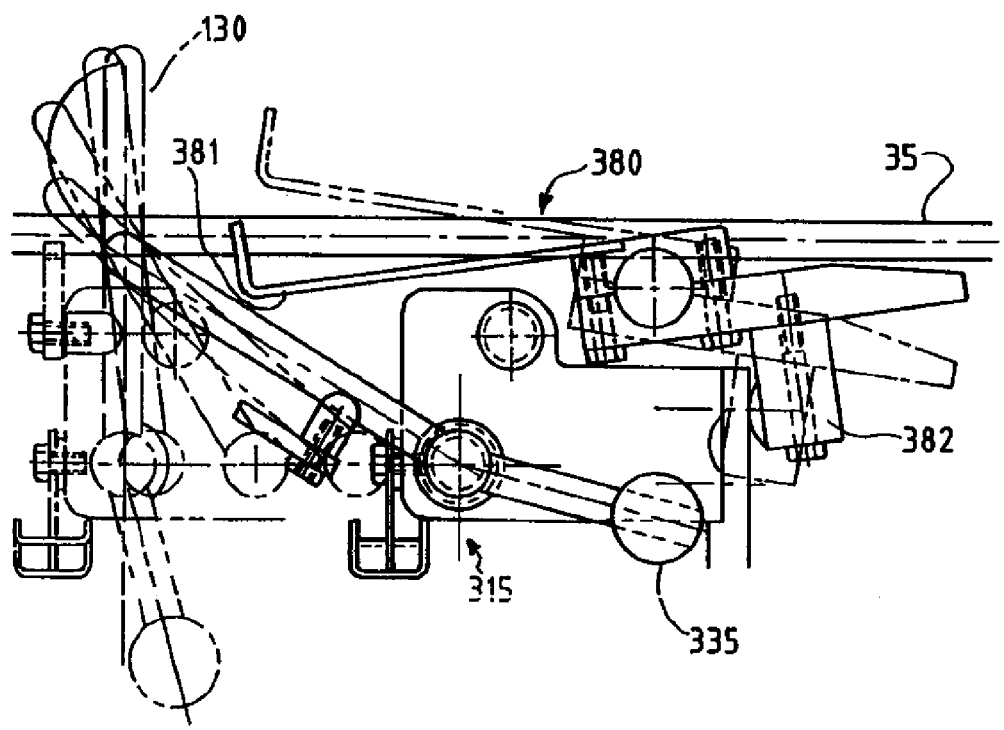
FIG. 7 is a schematic cross-sectional view showing a product stopper at the inlet to the vision system housing.

As a back-up precaution in the event the scanning section drive 350 gets ahead of the return movement of the fingers 130, there is preferably provided a product stop 380, shown in FIG. 7, which could hold the movement of the product under the influence of the engagement member 105 until the fingers 130 have fully returned to engage the next product. The product stopper 380 is freely pivotable about a transverse, horizontal axis, and formed at a forward side with an L-shaped stop wall 381 and on the other side of the pivot axis with a counterweight abutment 382. Until the piston carrying the fingers 130 is fully returned, the L-shaped stop wall 381 is in a raised blocking position in the path of conveyance of the next product being delivered to the vision system housing, as shown by the dotted line image in FIG. 7. With the piston in its fully-returned position, the counterweight abutment 382 is engaged and raised, causing the stop wall 381 to be lowered and not obstructing the conveyance movement of the next product. In this case, the engagement member 105 is able to conduct the product over the tilted-down fingers 130, as well as the lowered stop wall, and fully into the vision system housing for further conveyance, from behind, by the then raised fingers 130.

Other features of the specific embodiment that are shown in FIGS. 4 and 5 include reference reflectors 375. The reference reflectors 375 are those referenced above in connection with the operation of the profiling apparatus 15.

Numerous modifications may be made to the foregoing system without departing from the basic teachings thereof.

Although the present invention has been described in substantial detail with reference to one or more specific embodiments, those of skill in the art will recognize that changes may be made thereto without departing from the scope and spirit of the invention as set forth herein.

The invention claimed is:

1. An automated system for processing a food product based on the acquisition of the food product's surface profile, comprising:
   a product processor;
   a conveying device along which the product is conducted in sequence;
   a profiling apparatus having
      at least two upper line lasers disposed above the conveying device for illuminating an upper surface profile of the product,
      wherein the upper line lasers are adapted to illuminate the upper surface profile of the product across a first plane transverse to the conveyance direction of the product,
      wherein the upper liner lasers are disposed on opposite sides of the product for projecting laser beams onto and across the product;
      at least two lower line lasers disposed below the conveying device for illuminating a lower surface profile of the product,
      wherein the lower line lasers are adapted to illuminate the lower surface profile of the product across a second plane transverse to the conveyance direction of the product,
      wherein the lower liner lasers are disposed on opposite sides of the product for projecting laser beams onto and across the product;
      said profiling apparatus further having an upper camera located above the conveying device for imaging the upper surface profile illuminated by the upper line lasers, and
      a lower camera located below the conveying device for imaging the lower surface profile illuminated by the lower line lasers:
   a scale for weighing the product and for providing weight information;
   a controller being signal-connected to the upper and lower cameras, and to the scale, said controller being adapted for determining the volume of the product by acquiring and processing multiple visual images acquired by the upper and lower cameras along the length of the product as the product is moved through the profiling apparatus, and is arranged to complete acquiring and processing the multiple visual images of the product before processing of the product in the product processor; and
   wherein the product processor is a slicer adapted to cut slices of a particular weight, responsive to said controller and the product processor varies its processing operation on the product based upon the volume of the product and the weight information provided by the scale.

2. The system of claim 1, wherein the conveying device receives a stacked input of products, and conducts the input products successively and continuously.

3. The system of claim 1, wherein the multiple visual images are acquired at discrete increments along the length of the product.

4. The system of claim 1 wherein the conveying device comprises a scanning section drive that moves the product through said first transverse plane; and the scanning section drive is independent of the product processor.

5. The system of claim 1, wherein the conveying device comprises
   a scanning section drive and
   an output section drive, the scanning section drive moving the product through said first transverse plane to a position to be engaged by the output section drive for delivering the product into a loading position on the product processor.

6. The system of claim 1, wherein the conveying device comprises
   an input section drive for moving the product into the scanning section;
   a scanning section drive for moving the product through said first transverse plane to a position to be engaged by an output section drive for delivering the product out of the profiling apparatus.

7. The system of claim 1, wherein the profiling apparatus has reference markers in the first and second transverse planes for disposition on opposed sides of the product.

8. The system of claim 1,
   wherein the profiling apparatus has reference reflectors in the first and second transverse planes for disposition on opposed sides of the product, and
   wherein the upper and lower cameras acquire multiple visual images of the upper and lower surface profiles appearing as linear end regions corresponding to the reference reflectors and a plurality of vertically offset, non-linear regions between the linear end regions corresponding to the upper and lower surface profiles of the product.

9. An automated system for processing a food product based on the acquisition of the food product's surface profile, comprising:
   a product processor;
   a conveyor system along which the product is conducted in sequence;
   a profiling apparatus having
      at least two upper line lasers disposed above the conveyor system for illuminating the upper surface profile of the product,
      wherein the upper line lasers are adapted to illuminate the upper surface profile of the product across a fixed plane transverse to the conveyance direction of the product,
      wherein the upper liner lasers are disposed on opposite sides of the product for projecting laser beams onto and across the product;
      at least two lower line lasers disposed below the conveyor system for illuminating the lower surface profile of the product,
      wherein the lower line lasers are adapted to illuminate the lower surface profile of the product across the fixed plane transverse to the conveyance direction of the product,
      wherein the lower liner lasers are disposed on opposite sides of the product for projecting laser beams onto and across the product;
      said profiling apparatus further having an upper camera located above the conveyer system for imaging the upper surface profile illuminated by the upper line lasers, and
      a lower camera located below the conveyor system for imaging the lower surface profile illuminated by the lower line lasers;
   a scale for weighing the product and for providing weight information, said scale being included in the profiling apparatus;

a controller
being connected to the upper and lower cameras,
said controller being adapted for determining the volume of the product by acquiring and processing multiple visual images acquired by the upper and lower cameras along the length of the product as the product is moved through the profiling apparatus,
and is arranged to complete acquiring and processing the multiple visual images of the product before processing of the product in the product processor; and
wherein the product processor is a slicer adapted to cut slices of a particular weight,
said product processor comprising a control system that varies its processing operation on the product based upon the volume of the product and the weight information provided by the scale,
wherein the conveyor system conducts the product in sequence between the profiling apparatus and the product processor.

10. The system of claim 9, wherein the product is supported in the profiling apparatus on a plurality of spaced-apart bars extending parallel to the conveyed direction of the product.

11. The system of claim 10, wherein the bars are sized and shaped within the fixed plane to minimize obstruction of camera imaging of the product profile.

12. The system of claim 9, wherein the conveyor system receives a stacked input of products, and conducts the input products successively and continuously.

13. The system of claim 9, wherein the upper and lower cameras acquire a visual image of the upper and lower surface profiles appearing as linear end regions and a plurality of vertically offset non-linear regions between the linear end regions.

14. The system of claim 9, wherein the multiple visual images are acquired at discrete increments along the length of the product.

15. The system of claim 9, wherein the conveyor system comprises a scanning section drive that moves the product through said fixed plane, and the scanning section drive is independent of the product processor.

16. The system of claim 9, wherein the conveyor system comprises
a scanning section drive and
an output section drive, the scanning section drive moving the product through said fixed plane to a position to be engaged by the output section drive for delivering the product into a loading position on the product processor.

17. The system of claim 9, wherein the conveyor system comprises
an input section drive for moving the product into the scanning section;
a scanning section drive for moving the product through said fixed plane to a position to be engaged by an output section drive for delivering the product out of the profiling apparatus.

18. The system of claim 9, wherein the profiling apparatus has reference markers in the fixed plane for disposition an opposed sides of the product.

19. The system of claim 9,
wherein the profiling apparatus has reference reflectors in the fixed plane for disposition on opposed sides of the product, and
wherein the upper and lower cameras acquire multiple visual images of the upper and lower surface profiles appearing as linear end regions corresponding to the reference reflectors and a plurality of vertically offset, non-linear regions between the linear end regions corresponding to the upper and lower surface profiles of the product.

* * * * *